(12) United States Patent
Marques Abrantes et al.

(10) Patent No.: US 10,843,145 B2
(45) Date of Patent: Nov. 24, 2020

(54) METHOD AND DEVICE FOR PRODUCTION OF GRAPHENE OR GRAPHENE-LIKE MATERIALS

(71) Applicant: GRAPHENEST, S.A., Paradela SVV (PT)

(72) Inventors: Vitor Emanuel Marques Abrantes, Aveiro (PT); Bruno Reis Figueiredo, Bustos—Oliveira do Bairro (PT); Rui Pedro Fonseca Ferreira Da Silva, Macinhata do Vouga (PT)

(73) Assignee: GRAPHENEST, S.A., Paradela SVV (PT)

( * ) Notice: Subject to any disclaimer, the term of this patent is extended or adjusted under 35 U.S.C. 154(b) by 28 days.

(21) Appl. No.: 15/751,922

(22) PCT Filed: Aug. 11, 2016

(86) PCT No.: PCT/IB2016/054848
§ 371 (c)(1),
(2) Date: Feb. 12, 2018

(87) PCT Pub. No.: WO2017/025926
PCT Pub. Date: Feb. 16, 2017

(65) Prior Publication Data
US 2018/0229193 A1   Aug. 16, 2018

(30) Foreign Application Priority Data
Aug. 11, 2015   (PT) .......................................... 108765

(51) Int. Cl.
*C01B 32/184* (2017.01)
*B01F 7/00* (2006.01)
(Continued)

(52) U.S. Cl.
CPC ...... *B01F 7/00766* (2013.01); *B01F 13/1013* (2013.01); *B01J 19/0066* (2013.01);
(Continued)

(58) Field of Classification Search
CPC ............. B01F 7/00766; B01F 13/1013; C01B 32/184; C01B 32/19; C01B 32/225;
(Continued)

(56) References Cited

U.S. PATENT DOCUMENTS 5,330,680 A    7/1994 Sakawaki et al.
2009/0005587 A1    1/2009 Hassan et al.
(Continued)

FOREIGN PATENT DOCUMENTS

CN    101671015 A  *  3/2010
CN    102020270 A  *  4/2011
(Continued)

OTHER PUBLICATIONS

Varrla, Eswaraiah, et al. "Turbulence-assisted shear exfoliation of graphene using household detergent and a kitchen blender." Nanoscale 6.20 (2014): 11810-11819.*
(Continued)

*Primary Examiner* — Richard M Rump
(74) *Attorney, Agent, or Firm* — Leason Ellis LLP

(57) ABSTRACT

A method and a device for the production of graphene or graphene-like material are provided. The method can comprise the following steps: providing particles of a crystalline graphitic material; dispersing the particles in a solvent or surfactant mixture; submitting the mixture to a cavitation force such that cavitation bubbles are present; and submitting the mixture to high shear agitation. The cavitation and high shear agitation steps can be simultaneous, in particular in the same enclosed vessel. The device for the production of graphene or graphene-like material can comprise a reactor
(Continued)

having an enclosed vessel for receiving a solvent or surfactant mixture with dispersed particles of a crystalline graphitic material. The reactor can be arranged for: submitting the mixture in the enclosed vessel to a cavitation force such that cavitation bubbles are present and, simultaneously in the same enclosed vessel, submitting the mixture to high shear agitation.

13 Claims, 1 Drawing Sheet

(51) Int. Cl.
 *C01B 32/19* (2017.01)
 *C01B 32/194* (2017.01)
 *C01B 32/225* (2017.01)
 *B01F 13/10* (2006.01)
 *B01J 19/00* (2006.01)
 *C01G 39/06* (2006.01)
 *C07C 67/08* (2006.01)
(52) U.S. Cl.
 CPC ............ *C01B 32/184* (2017.08); *C01B 32/19* (2017.08); *C01B 32/194* (2017.08); *C01B 32/225* (2017.08); *C01G 39/06* (2013.01); *C07C 67/08* (2013.01)
(58) Field of Classification Search
 CPC ....... C01B 32/194; C07C 67/08; C01G 39/06; B01J 19/0066
 See application file for complete search history.

(56) References Cited

U.S. PATENT DOCUMENTS

| | | |
|---|---|---|
| 2013/0001068 A1 | 1/2013 | Zhamu et al. |
| 2014/0242275 A1 | 8/2014 | Zhamu et al. |

FOREIGN PATENT DOCUMENTS

| | | | |
|---|---|---|---|
| CN | 102757035 A | | 10/2012 |
| CN | 103553030 A | | 2/2014 |
| CN | 103632845 A | | 3/2014 |
| CN | 103754864 A | | 4/2014 |
| CN | 104058393 A | * | 9/2014 |
| WO | 2013106963 A1 | | 7/2013 |
| WO | 2014140324 A1 | | 9/2014 |

OTHER PUBLICATIONS

Alaferdov et al. "Size-controlled synthesis of graphite nanoflakes and multi-layer graphene by liquid phase exfoliation of natural graphite." Carbon 69 (2014): 525-535.

Han et al. "Extremely efficient liquid exfoliation and dispersion of layered materials by unusual acoustic cavitation." Scientific Reports 4 (2014): 5133. 7 pages.

* cited by examiner

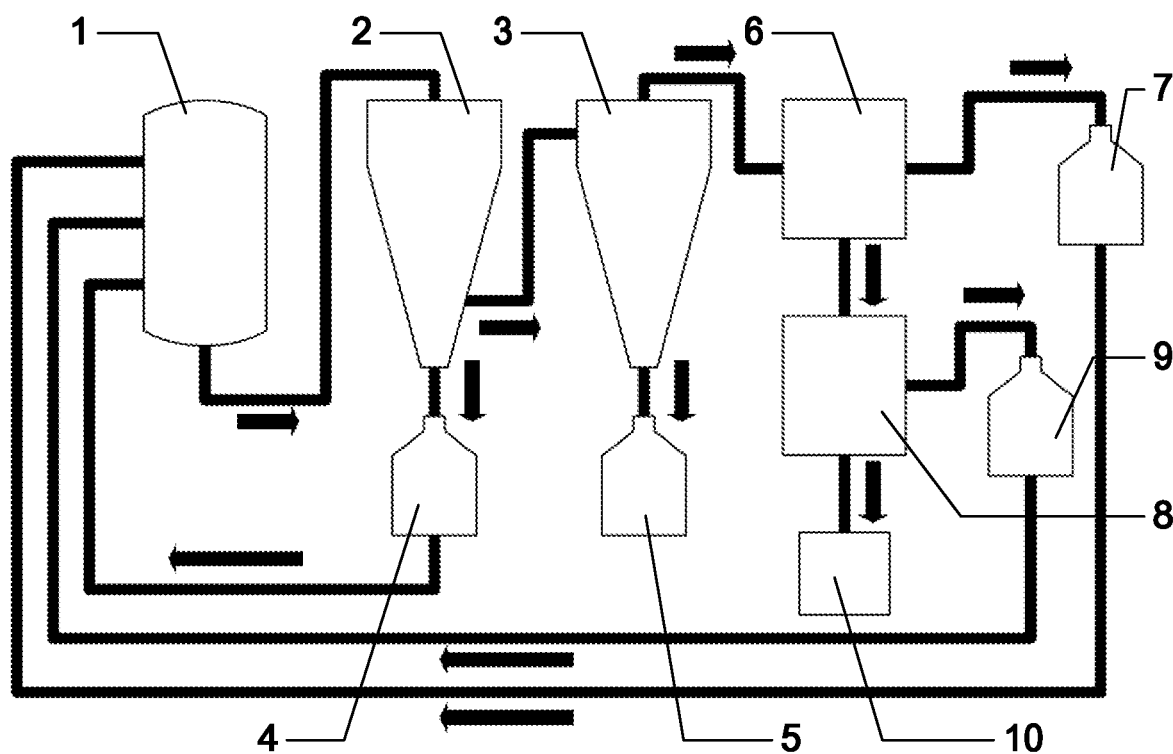

METHOD AND DEVICE FOR PRODUCTION OF GRAPHENE OR GRAPHENE-LIKE MATERIALS

CROSS-REFERENCE TO RELATED APPLICATIONS

This application is a U.S. National Stage Application under 35 U.S.C. § 371 of International Patent Application No. PCT/IB2016/054848 filed on Aug. 11, 2016, which claims priority to Portuguese Patent Application No. 108765 filed on Aug. 11, 2015, both of which are hereby incorporated by reference in their respective entireties.

TECHNICAL FIELD

The present disclosure relates to a method and device for producing graphene sheets, graphene-like sheet materials, in particular metal dichalcogenides, oxides and carbides, or two-dimensional or few-layer nano-materials.

BACKGROUND

Graphene is a known two-dimensional material composed of an atomic-scale honeycomb lattice made of carbon atoms. It possesses distinct properties that makes of it a promising material for several applications. Specifically, its high conductivity capacity may encounter applicability in sensors, batteries, transistors, capacitors, among others. Since the production of graphene by mechanical exfoliation or peeling, a wide range of graphene synthesis techniques have emerged. Graphene production process can be currently achieved by one of the following methods.

The document CN102757035A describes a method to obtain high-purity graphene through the combination of a solvent, such as dimethylformamide, thermal treatment and microwave methods. The obtaining process began with the preparation of a graphite solution that was heat-treated by microwave. Then, the solvent was removed and the resultant material was filtrated and washed, followed by a drying process. The performance rate of this method is about 10-15%. However, the method and device that is presently disclosed does not include any heat-treatment by microwave and has a much higher performance.

The document CN103632845A describes a method to obtain a graphene/organic thin film composite. The procedure started with an uncontrolled ultrasonic dispersion of a graphite oxide/solvent mixture in order to obtain a liquid graphene oxide suspension. It is claimed that the preferable solvents are deionized water, ethanol, isopropanol or n-butanol. Then, the pH of the solution is adjusted between values of 10 and 11 and a hydrazine hydrate solution is added to the suspension. After several filtrations, a graphene suspension is obtained and further used to coat an organic thin film. After drying, the process of roller pressing is performed and repeated after the soaking of the mixed solution of acetone and isopropyl alcohol, so as to acquire the graphene/organic thin film composite. However, the presently disclosed method and device do not have an uncontrolled ultrasonic dispersion of a graphite oxide/solvent mixture in order to obtain a liquid graphene oxide suspension.

Another method for the preparation of graphene is disclosed in the document CN103754864A where a graphene film is obtained as a layer on a quartz slide. For that, polymethyl methacrylate (PMA) was dissolved in ketone and added on a metal sheet, forming a film layer of polymethyl methacrylate. A quartz glass film was covered with the PMA film. For that, the metal sheet, the PMA film on the metal sheet and the quartz glass slide were placed simultaneously into a high-temperature annealing furnace with a nitrogen atmospheric condition. High-temperature annealing, from 800 to 1000° C. was performed leading the PMA to decompose into a graphene film under the catalytic action of the metal in the metal film. The graphene film evaporated at high temperature and was transferred to the quartz glass slide. The spontaneous cooling until room temperature resulted in the graphene film. However, this method uses PMA unlike the presently disclosed method and device.

The document US20130001068A1 discloses a combined production-functionalization process for the obtainment of chemically functionalized graphene material. The disclosed method declares that is possible to obtain graphene by exfoliating pre-intercalated, oxidized, or halogenated graphite. Furthermore, the document also claimed that the graphite material may be selected from a group consisting of natural graphite, artificial graphite, highly oriented pyrolytic graphite, carbon fiber, graphite fiber, carbon nanofiber, graphitic nanofiber, meso-carbon micro-bead, graphitized coke, and combinations thereof. The graphene production was initiated by the dispersion of the exfoliated graphite and an azide or bi-radical compound in a liquid medium to form a suspension. Then, this suspension was subjected to ultrasonic waves of a desired intensity for a period sufficient to produce nanographene platelets and to trigger a chemical reaction between the nanographene platelets and the azide, producing the wanted functionalized material. However, this method uses an aqueous suspension with azide or bi-radical compounds that are going to react with the graphite nanoplatelets, unlike the presently disclosed method and device.

Until now, strong acids and oxidants were used in graphene production, which implied future separation and purification after synthesis. Furthermore, due to the volatile character of the reagents and their combination with the exothermic nature of the reaction, such chemicals render the process more challenging and expensive, implying tighter restrictions in both security and environmental management. Moreover, the already existing synthesis processes can contribute to the deterioration of the graphene structure, which will ultimately lead to a quality reduction. Additionally, the separation process of the resulting final product has also a high associated cost that becomes imperative to reduce.

These facts are disclosed in order to illustrate the technical problem addressed by the present disclosure.

GENERAL DESCRIPTION

It is described a method for the production of graphene, graphene-like and other two-dimensional materials, comprising the following steps:
1—providing a crystalline graphitic material;
2—disperse the particles of graphite in a solvent or surfactant mixture;
3—submit the mixture to a cavitation force containing cavitation bubbles;
4—submit the mixture to high shear agitation in the range of 2000 to 35000 RPM;
5—submit the mixture to an atomization nozzle and spray drying process.

Graphene-like materials may be defined as two-dimensional or few-layer nano-materials, in particular metal dichalcogenides, oxides and carbides.

In an embodiment, the crystalline graphitic material used in the method for the production of graphene, graphene-like and other two-dimensional material is introduced with a quantity of 0.25 to 1.25 mg/mL.

In an embodiment, the crystalline graphitic material used in the method for the production of graphene, graphene-like and other two-dimensional material is selected from the group composed by natural graphite, pyrolytic graphite, meso-carbon micro-bead carbon or graphite fiber, carbon or graphitic nano-fiber, soft carbon, hard carbon, and combinations thereof.

In an embodiment, the solvent or surfactant used in the second step of the method for the production of graphene, graphene-like and other two-dimensional material is selected from at least one of the following: butyl alcohol, ethanol, acetone, petroleum ether, N-methylpyrrolidone, hydrogen peroxide and water.

In an embodiment, the mixture in the third step of the method for the production of graphene, graphene-like and other two-dimensional material is subject to a cavitational force.

In an embodiment, the cavitation bubbles used in the method for the production of graphene, graphene-like and other two-dimensional material comprise a radius size within a range of 0.2 to 18 μm. This can be determined by the system operating conditions or through cavitation meters by measuring locally the energy of each bubble.

In an embodiment, the fourth step of the method for the production of graphene, graphene-like and other two-dimensional material is made in at least two dispersion elements.

In an embodiment, the dispersion elements of the method for the production of graphene, graphene-like and other two-dimensional material are a rotor and a stator.

In an embodiment, the spray drying process used in the method for the production of graphene, graphene-like and other two-dimensional material is made on a spray drying chamber, a cyclone, a dehumidifier and an inert loop.

In an embodiment, the fifth step of the method for the production of graphene, graphene-like and other two-dimensional material is made at temperatures comprised between 40 and 350° C.

The present application describes a method for producing graphene sheets, graphene-like materials and other two-dimensional materials that combines high shear thermomechanical exfoliation methods. A modular equipment associates four distinct effects in the same enclosed vessel: chemical, thermal, mechanical and cavitational. The cavitation is the governing effect being aided by one, at least, of the others. The chemical and mechanical effects are of great importance to establish the best hydrodynamic properties and therefore reduce production time, what gives them an important role as cavitational-combinatorial effects.

This new method allows a much smaller production cost, higher control of defects in the structure of the material, less hazardous to human beings, animals and environment and feasibility to scale-up. For example, the production cost is significantly lower than conventional methods, like the modified Hummers method or the chemical vapor deposition (CVD) that usually are very ineffective and extensives. Controlling the energy of the bubbles implosions generated by the cavitational effect permits to have a higher control of defects in the structure which turns also possible to obtain tailor-made materials according to the customers and market needs, which represents a great novelty.

The method now disclosed is environmentally friendly since it does not use strong oxides or acids, an important advantage in the modern World.

The present application discloses a method for the production of graphene, graphene-like and other two-dimensional materials, said method comprising the following steps:
1—providing a crystalline graphitic material;
2—disperse the particles of the crystalline graphitic materials from the previous step in a solvent or surfactant;
3—submit the mixture obtained in the previous step to a cavitational force containing cavitation bubbles, which can have a radius in the range of 0.2 to 18 microns; in order to achieve exfoliation of graphite until complete flatness and ultimately produce graphene a large number of implosions of controlled size and therefore energy is required to archive the desired effect;
4—submit the mixture obtained in the second step to a high shear agitation in the range of 2000 to 35000 RPM at the same time of the third step;
5—submit the mixture of the second, third and fourth steps to an atomization nozzle and spray drying process.

The production method described above may be also applied for the production of other two-dimensional (2D) materials from the following group: boron nitride, germanene, silicene, stanene, phosphorene, molybdenum disulfide and tungsten disulfide, by replacing the crystalline graphitic material with the corresponding precursor material of the desired 2D material.

This description also relates to graphene obtained by such method, which has a much lower level of structural defects.

It is disclosed a method for the production of graphene or graphene-like material, comprising the following steps:
providing particles of a crystalline graphitic material;
dispersing the particles of the crystalline graphitic material in a solvent mixture, or surfactant mixture, or a solvent and surfactant mixture;
submitting the mixture to a cavitation force such that cavitation bubbles are present;
submitting the mixture to high shear agitation of 2000 to 35000 RPM.

In an embodiment, the cavitation step and the high shear agitation step are simultaneous, further in particular wherein the cavitation step and the high shear agitation step are simultaneous in the same enclosed vessel.

In an embodiment, the crystalline graphitic material is provided at 0.25 to 25 mg/mL, in particular 0.25 to 15 mg/mL, further in particular 0.25 to 1.25 mg/mL.

In an embodiment, the cavitation bubbles have a radius size within a range of 0.2 to 18 μm, in particular 1.2 to 10.5 μm, further in particular 2.4 to 6.8 μm.

In an embodiment, the cavitation force is modulated in working frequency of a 1-5% range, in particular 3%, of a sweep function.

In an embodiment, the high shear agitation of the method is made by at least two mechanical dispersion elements.

In an embodiment, the mechanical dispersion elements are a rotor and a stator.

In an embodiment, the rotor and stator are arranged for creating a double toroidal vortex with shear stirring with doppler effect.

In an embodiment, the high shear agitation is 5000 to 15000 RPM, in particular 6500 to 10500 RPM.

In an embodiment, the crystalline graphitic material is selected from: natural graphite, pyrolytic graphite, meso-carbon micro-bead carbon or graphite fiber, carbon or graphitic nano-fiber, soft carbon, hard carbon, or combinations thereof.

In an embodiment, the solvent or surfactant is selected from: butyl alcohol, ethanol, acetone, ketone, petroleum ether, N-methylpyrrolidone, hydrogen peroxide, water, or mixtures thereof.

In an embodiment, the solvent or surfactant mixture has a Hildebrand solubility of at least of 23 $MPa^{(1/2)}$.

In an embodiment, the cavitation step and the high shear agitation step are carried out for 0.1 to 12 hours.

An embodiment comprises a subsequent step of submitting the mixture to an atomization nozzle and spray drying process.

In an embodiment, the spray drying process is made on a spray drying chamber, a cyclone, a dehumidifier and an inert loop.

In an embodiment, the atomization nozzle and spray drying process step is made at temperatures comprised between 40 and 350'C.

It is disclosed a device for the production of graphene or graphene-like material, comprising a reactor having an enclosed vessel for receiving a solvent or surfactant mixture with dispersed particles of a crystalline graphitic material, said reactor being arranged for:

submitting the mixture in the enclosed vessel to a cavitation force such that cavitation bubbles are present and, simultaneously in the same enclosed vessel, submitting the mixture to high shear agitation of 2000 to 35000 RPM.

In an embodiment, the reactor is configured for producing cavitation bubbles having a radius size of 0.2 to 18 μm, in particular 1.2 to 10.5 μm, further in particular 2.4 to 6.8 μm.

An embodiment comprises two mechanical dispersion elements for high shear agitation.

In an embodiment, the mechanical dispersion elements are a rotor and a stator.

In an embodiment, the rotor and stator are arranged for creating a double toroidal vortex with shear stirring with doppler effect.

In an embodiment, the high shear agitation is 5000 to 15000 RPM, in particular 6500 to 10500 RPM.

An embodiment comprises an atomization nozzle and spray drying stage for subsequent spray drying of the mixture.

An embodiment comprises a spray drying chamber, a cyclone, a dehumidifier and an inert loop.

BRIEF DESCRIPTION OF THE DRAWINGS

The following FIGURE provides a preferred embodiment for illustrating the description and should not be seen as limiting the scope of invention.

FIG. 1: Schematic representation of an embodiment of the disclosed reactor used in the method for the production of graphene, graphene-like and others two-dimensional materials.

DETAILED DESCRIPTION

It is disclosed a method for the production of graphene, graphene-like and other two-dimensional materials, said method comprising the following steps:
1—providing a crystalline graphitic material;
2—disperse the particles of graphite in a solvent or surfactant mixture;
3—submit the mixture to a cavitation force containing cavitation bubbles, which can have a radius in the range of 0.2 to 18 μm;
4—submit the mixture to high shear agitation in the range of 2000 to 35000 RPM;
5—submit the mixture to an atomization nozzle and spray drying process.

In an embodiment, the graphitic materials used in the first step of the above mentioned method are selected from the group composed by natural graphite, pyrolytic graphite, meso-carbon micro-bead carbon or graphite fiber, carbon or graphitic nano-fiber, soft carbon, hard carbon, and combinations thereof. These graphitic materials are introduced with a quantity of 0.25 to 1.25 mg/mL, preferably 0.5 mg/mL.

In an embodiment, the solvent or surfactant used in the second step of the method is selected from at least one of the following: butyl alcohol, ethanol, acetone, petroleum ether, N-methylpyrrolidone, hydrogen peroxide and water.

In the second step of the method, the intention is to lower the surface tension and Hildebrand solubility parameter during the process in order to enhance the thermomechanical system and decrease the energy of the colloidal dispersion. The energetic cost of the exfoliation goes lower as soon as we have a Hildebrand solubility of 23 $MPa^{(1/2)}$, which means, a surface tension of 40 $mJ/m^2$.

Then, in the third step of the method, the mixture is subject to a cavitational force, a very well-known phenomenon that generates vapour cavities in the liquid medium or liquid-cavitation-free zones where the rapid change of pressure cause the formation of said cavities because the pressure in that zone is relatively lower. The cavities are also called cavitation bubbles, implosion bubbles or voids and in this application the bubbles comprise a radius size within a range of 0.2 to 18 μm. In order to achieve exfoliation of graphite until complete flatness and ultimately produce graphene a large number of implosions of controlled size and therefore energy is required to archive the desired effect. In the formation of cavitation bubbles, also called non-inertial cavitation, the bubbles oscillates in size, storing energy until it is released in the form of a jet and shock wave. The energy jets that occur near the particle surface allow a smooth break of the van der Waals bonds between graphite layers. The generated bubbles implodes or collapses on themselves creating local conditions of 5000 degrees Celsius and 50 MPa of pressure. Due to the boundary layer effect, large sized bubbles are not allowed to form close enough to the convoluted surface, which due to their high energy characteristic have a destructive structural impact generating defects on the produced graphene. However, smaller cavitation bubbles are able to penetrate the interlayers surface enabling the peeling of each layer without damaging the graphene structure, nor adding defects. A noteworthy aspect of the disclosed method is that the doppler effect of the high shear stirring, enhanced the performance in particle movement or particle momentum, which also uniforms the wave interference through the particle flow, thus enabling further control and optimization of the graphene production. This third step is made in about 0.1 to 12 h.

In the fourth step of the method, it may be used at least two dispersion elements, a rotor and a stator, mounted in a pivot. The rotor or impeller is used in combination with the stationary component known as a stator to create a shear force that generates a double toroidal vortex to achieve the desired results. The latter promotes a high mechanical stress in the material, breaking it down into small particles or microparticles. The stirred method will be able to create a double flow vortex that split or break the bigger particles, with at least 200 μm, into small ones within a range of 10 to 30 μm. The combination (simultaneous) of high shear agitation and cavitation force, described in the third step, helps improving the production efficiency by reducing the time-cycle, homogenizing the mixture or lower range of particle size and avoid standing waves in the liquid medium.

The mixture is then submitted to an atomization nozzle and spray drying process on a spray drying chamber, a cyclone, a dehumidifier and an inert loop. The spray drying process transforms a pumpable fluid feed into a dried product in a single operation, separating solids and gases. The fluid is atomized using a rotating wheel or a nozzle where the spray of droplets immediately comes into contact with a flow of hot drying medium, usually air.

The resulting rapid evaporation maintains a low droplet temperature so that high drying air temperatures can be applied without affecting the material. The evaporation rate is usually about 6 kg/h for water (only one atomizer) and is considerably more for organic solvents where a gain of 50% may be achieved. The droplets drying time is very short in comparison with most other drying processes. Low product-temperature and short drying-time allow spray drying of very heat-sensitive materials like graphene.

As can be seen in FIG. 1, the solvent/graphene mixture obtained with the described method is pumped with air from the reactor vessel for exfoliation of graphitic materials (1) using a high pressure two fluid nozzle and injected into the spray drying chamber (2) that converts the mixture and the air gas into a cloud of droplets that contact the hot drying gases. The feed ratio with higher flow volume of gas, comprised in range between 50 to 90%, generally produces smaller average particle sizes.

The cyclone (3) removes the finest particulates from an air, gas or liquid stream, without the use of filters, through vortex separation. Then, the final solid product drops to the finish product collector (5) and the gases separated. Specifically, water is separated by the dehumidifier (6) and transferred to a proper water collector (7) while the inert loop (8) condensates the gases that are transferred into a different solvent collector (9). The carrier gas flow to treat the evaporation of about 6 kg/h of water shall be about 80 kg/h.

After separation, the final product is held and the condensed fluids may be reused on the next production batch. In the fifth step, the temperature for submitting the mixture to an atomization nozzle and spray drying process on a spray drying chamber, a cyclone, a dehumidifier and an inert loop is comprised between 40 and 350° C.

FIG. 1 illustrates an embodiment of the reactor used in the method for the production of graphene, graphene-like and other two-dimensional materials, where the following are represented: 1—Reactor vessel for exfoliation of graphitic materials; 2—Spray drying chamber; 3—Cyclone; 4—Large particles collector; 5—Finish product collector; 6—Dehumidifier; 7—Water collector; 8—Inert loop; 9—Solvent collector; 10—Exhaust air with particle filter.

The following pertains to experimental data and representative results. During the development of this technology, it has been prepared graphene sheets using ketone/water mixture as solvent.

The reaction mixture has been prepared by dispersing 100 grams of natural graphite flakes, with average particle size of at least 200 μm, in 5 liters of ketone/water mixture with a molar ratio 75/25.

Then, the mixture is submitted to a cavitation force with an implosion bubble radius size of 1.33 μm and modulated in working frequency of a 3% range by a 'sweep' function, during 30 minutes and with a temperature of 40 degrees Celsius.

The power intensity is established in the value of 30 watt/liter. At the same time and in the same enclosed vessel, the mixture is submitted to a high shear agitation of 7500 RPM.

Finally, the mixture is submitted to a spray drying process during two hours, until complete drying and separation of the graphene sheets from the mixture. The solvents are recovered and able to use in new production batch.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

This description is of course not in any way restricted to the embodiments presented herein and any person with an average knowledge of the area can provide many possibilities for modification thereof without departing from the general idea as defined by the claims.

The embodiments described above can be combined with each other. The following claims further define particular embodiments of the disclosure.

The invention claimed is:

1. A method for the production of graphene or graphene-like material, comprising the following steps:
   providing particles of a crystalline graphitic material;
   dispersing the particles of the crystalline graphitic material in a solvent mixture or surfactant mixture to form a mixture;
   submitting the mixture to a cavitation force such that cavitation bubbles are present;
   submitting the mixture to high shear agitation of 2000 to 35000 RPM; and
   submitting the mixture to an atomization nozzle and spray drying process, wherein the spray drying process is conducted via a spray drying chamber, a cyclone, a dehumidifier and an inert loop.

2. The method of claim 1, wherein the steps of submitting the mixture to the cavitation force and submitting the mixture to high shear agitation are simultaneous, and are performed in a single enclosed vessel.

3. The method of claim 1, wherein the crystalline graphitic material is provided at 0.25 to 25 mg/mL.

4. The method of claim 1, wherein the cavitation bubbles have a radius size within a range of 0.2 to 18 μm.

5. The method of claim 1, wherein the cavitation force is modulated in working frequency of a 1-5% range of a sweep function.

6. The method of claim 1, wherein the high shear agitation of the method is made by at least two mechanical dispersion elements, wherein the mechanical dispersion elements comprise a rotor and a stator.

7. The method of claim 6, wherein the rotor and stator are arranged for creating a double toroidal vortex with shear stirring with doppler effect.

8. The method of claim 1, wherein the high shear agitation is 5000 to 15000 RPM.

9. The method of claim 1, wherein the crystalline graphitic material is selected from the group consisting of: natural graphite, pyrolytic graphite, meso-carbon micro-bead carbon or graphite fiber, carbon or graphitic nano-fiber, soft carbon, hard carbon, and combinations thereof.

10. The method of claim 1, wherein the solvent mixture or surfactant mixture comprises a compound is-selected from the group consisting of: butyl alcohol, ethanol, acetone, ketone, petroleum ether, N-methylpyrrolidone, hydrogen peroxide, water, and mixtures thereof.

11. The method of claim 1, wherein the solvent mixture or surfactant mixture has a Hildebrand solubility of at least of 23 $MPa^{(1/2)}$.

12. The method of claim 1, wherein the steps of submitting the mixture to the cavitation force and submitting the mixture to high shear agitation are carried out for 0.1 to 12 hours.

13. The method of claim 1, wherein the atomization nozzle and spray drying process step is made at temperatures comprised between 40 and 350° C.

* * * * *